(12) United States Patent
Park et al.

(10) Patent No.: US 11,771,204 B2
(45) Date of Patent: Oct. 3, 2023

(54) METHOD FOR MANUFACTURING MASK PACK FOR ADSORBING HEAVY METALS, AND MASK PACK MANUFACTURED THEREBY

(71) Applicants: LG CHEM, LTD., Seoul (KR); LG HOUSEHOLD & HEALTH CARE LTD., Seoul (KR)

(72) Inventors: Minsung Park, Daejeon (KR); Haesung Yun, Daejeon (KR); Juhan Kim, Daejeon (KR); Wonjae Lee, Daejeon (KR); Kwang Seoung Jeon, Daejeon (KR); Seul Gi Kang, Daejeon (KR); Seung Min Oh, Suwon-si (KR); Ji Ung Park, Daejeon (KR)

(73) Assignees: LG CHEM, LTD., Seoul (KR); LG HOUSEHOLD & HEALTH CARE LTD., Seoul (KR)

(*) Notice: Subject to any disclaimer, the term of this patent is extended or adjusted under 35 U.S.C. 154(b) by 725 days.

(21) Appl. No.: 16/758,497

(22) PCT Filed: Dec. 11, 2018

(86) PCT No.: PCT/KR2018/015665
§ 371 (c)(1),
(2) Date: Apr. 23, 2020

(87) PCT Pub. No.: WO2019/117582
PCT Pub. Date: Jun. 20, 2019

(65) Prior Publication Data
US 2020/0253358 A1 Aug. 13, 2020

(30) Foreign Application Priority Data
Dec. 14, 2017 (KR) .................. 10-2017-0171982
Dec. 6, 2018 (KR) .................. 10-2018-0156084

(51) Int. Cl.
A45D 44/00 (2006.01)
A61K 8/02 (2006.01)
A45D 44/22 (2006.01)
A61Q 19/00 (2006.01)
D21H 13/04 (2006.01)

(52) U.S. Cl.
CPC .......... *A45D 44/002* (2013.01); *A61K 8/0212* (2013.01); *A45D 44/22* (2013.01); *A45D 2200/1036* (2013.01); *A61Q 19/00* (2013.01); *D21H 13/04* (2013.01)

(58) Field of Classification Search
CPC ...................................... A45D 44/22
See application file for complete search history.

(56) References Cited

U.S. PATENT DOCUMENTS

| 9,481,963 B2 | 11/2016 | Im et al. |
| 2008/0147033 A1 | 6/2008 | Luo et al. |
| 2010/0042034 A1 | 2/2010 | Riesinger |

FOREIGN PATENT DOCUMENTS

| CN | 106699901 A | 5/2017 |
| KR | 10-0483808 B1 | 6/2003 |
| KR | 10-1361629 B | 2/2014 |
| KR | 10-1559815 B | 4/2014 |
| KR | 101437082 B1 | 7/2014 |
| KR | 10-2014-0113615 A | 9/2014 |
| KR | 10-1607939 B1 | 11/2015 |
| KR | 10-1747674 B1 | 1/2017 |
| KR | 2017-0005346 A | 1/2017 |
| KR | 10-1309847 B1 | 7/2017 |
| KR | 10-2017-0099316 A | 8/2017 |
| KR | 10-2017-0099572 A | 9/2017 |

OTHER PUBLICATIONS

International Search Report Issue for International Application No. PCT/KR2018/015665 dated Mar. 21, 2019, 5 pages.
Supplementary European Search Report in EP1888621 dated Jul. 8, 2020, 6 pages.

*Primary Examiner* — Gina C Justice
(74) *Attorney, Agent, or Firm* — ROTHWELL, FIGG, ERNST & MANBECK, P.C.

(57) ABSTRACT

Provided are a method for manufacturing a mask pack for heavy metal adsorption comprising immersing a cellulose nonwoven fabric in an alkali solution by a cold pad batch method and then aging the cellulose nonwoven fabric at room temperature for 10 minutes to 50 minutes, and immersing the cellulose nonwoven fabric in a carboxymethylation solution by the cold pad batch method and then aging the cellulose nonwoven fabric at room temperature to 60° C. for 10 minutes to 3 hours, and a mask pack for heavy metal adsorption manufactured by the method.

14 Claims, 3 Drawing Sheets

[FIG. 1]
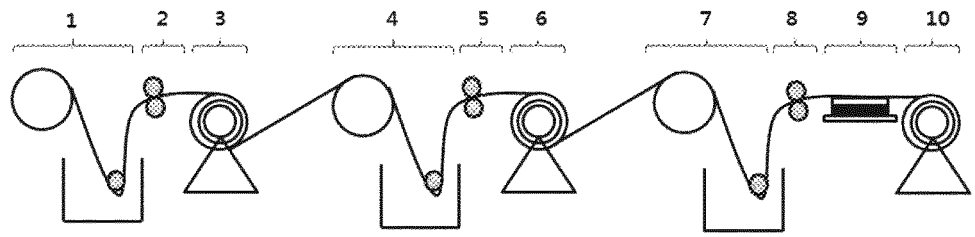
[FIG. 2]
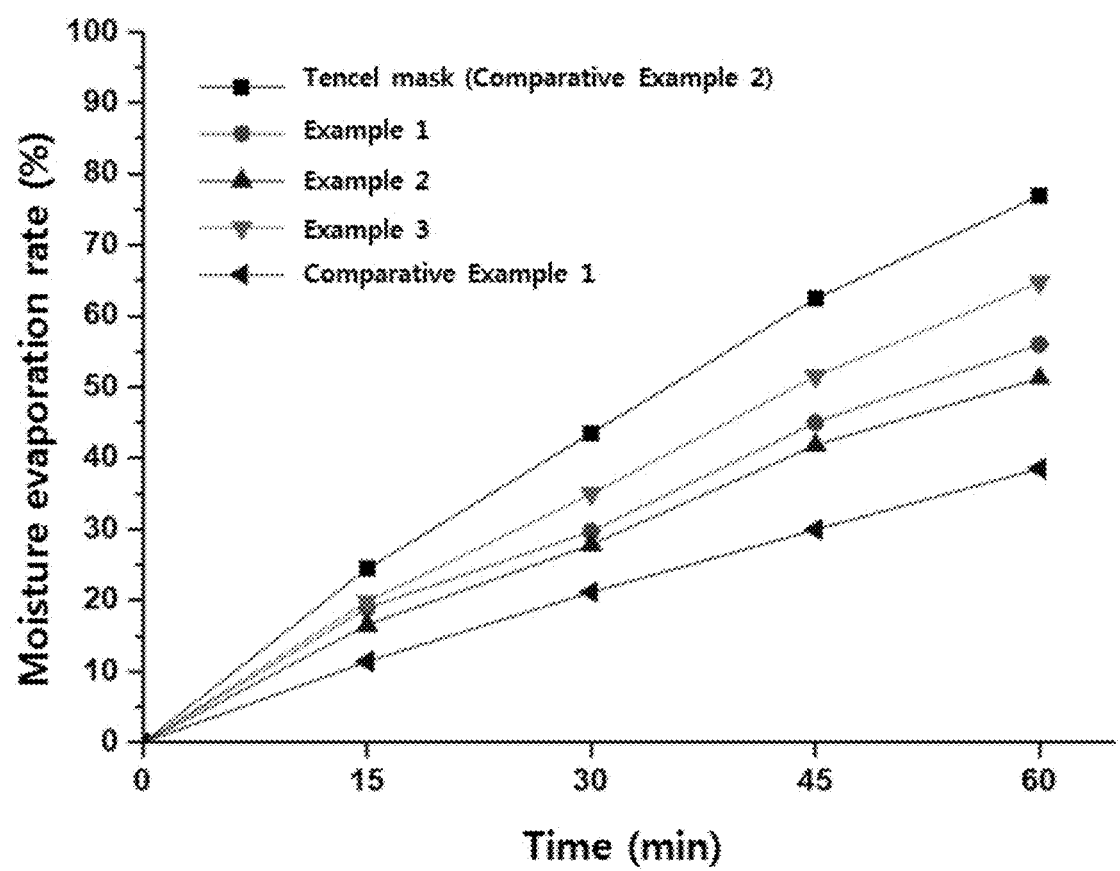

[FIG. 3]
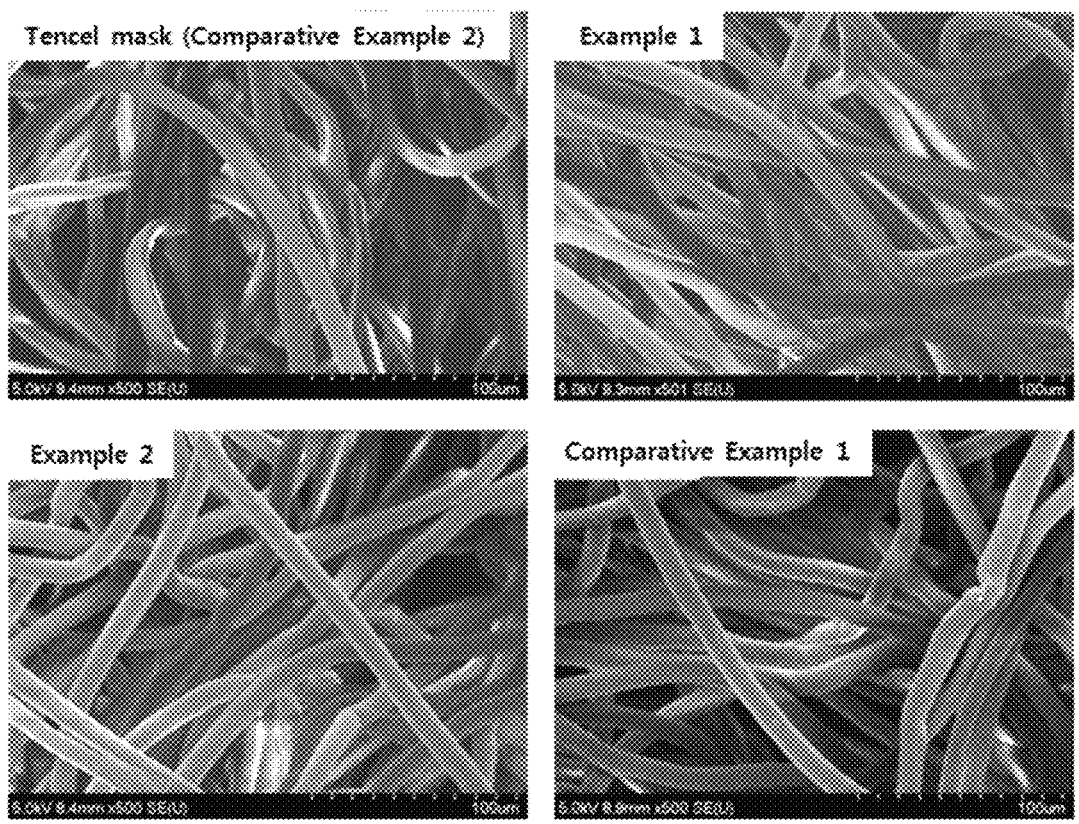

[FIG. 4]
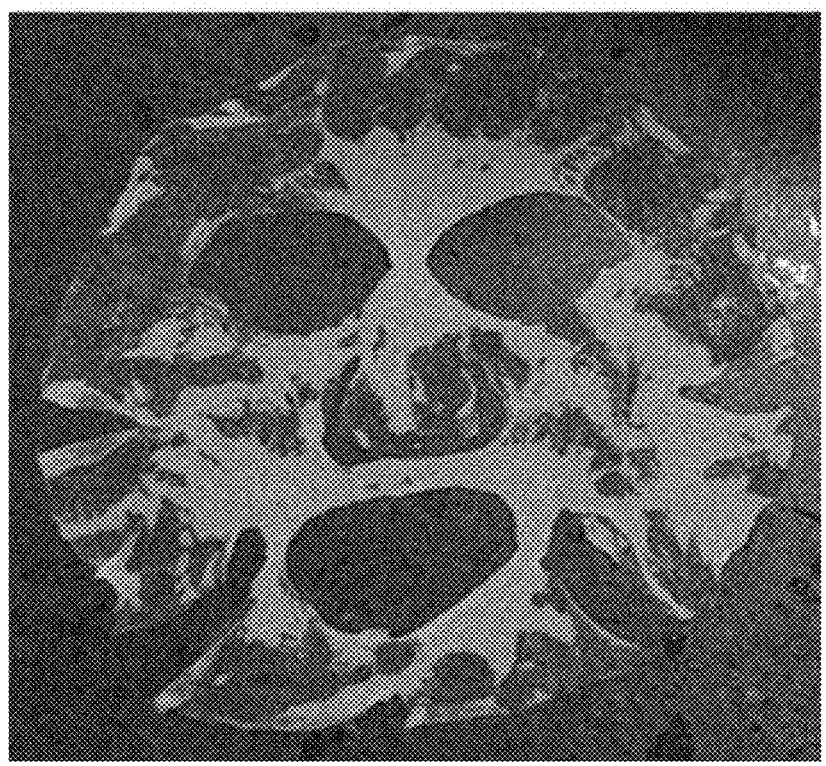

METHOD FOR MANUFACTURING MASK PACK FOR ADSORBING HEAVY METALS, AND MASK PACK MANUFACTURED THEREBY

The present application is a 35 U.S.C. § 371 National Phase Entry Application from PCT/KR2018/015665, filed on Dec. 11, 2018, and designating the United States, which claims priority to and the benefits of Korean Patent Application No. 10-2017-0171982, filed with the Korean Intellectual Property Office on Dec. 14, 2017 and Korean Patent Application No. 10-2018-0156084, filed with the Korean Intellectual Property Office on Dec. 6, 2018, the entire contents of which are incorporated herein by reference.

The present disclosure relates to a method for manufacturing a mask pack for heavy metal adsorption and a mask pack manufactured by the same.

BACKGROUND OF THE INVENTION

Fine dust, which has recently emerged as an important environmental issue, contains a large amount of heavy metals that cause diseases. Although studies on air filters and water treatment filters have been actively made to protect the human body from such heavy metals, studies associated with removal of heavy metals directly adhered to the skin are insufficient.

A mask pack is a cosmetic that surrounds the face and supplies moisture and cosmetic ingredients to the skin to clean the skin and restore the skin's physiological functions. In order to remove heavy metals directly adhered to the skin using such a mask pack, a mask pack is manufactured by adding a substance capable of adsorbing heavy metals.

However, a simple method including addition and mixing of such a substance has a limitation in increasing heavy metal adsorption performance and causes problems of low economic efficiency due to expensive adsorbable substance.

In order to overcome such problems, there is a need for research on mask packs capable of efficiently adsorbing heavy metals.

The present disclosure is directed to providing a method for manufacturing a mask pack for heavy metal adsorption and a mask pack manufactured by the same.

One embodiment of the present disclosure provides a method for manufacturing a mask pack for heavy metal adsorption comprising immersing a cellulose nonwoven fabric in an alkali solution by a cold pad batch method and then aging the cellulose nonwoven fabric at room temperature for 10 minutes to 50 minutes, and immersing the cellulose nonwoven fabric in a carboxymethylation solution by the cold pad batch method and then aging the cellulose nonwoven fabric at room temperature to 60° C. for 10 minutes to 3 hours.

Also, another embodiment of the present disclosure provides a mask pack for heavy metal adsorption manufactured by the method described above.

Advantageous Effects

The mask pack for heavy metal adsorption manufactured by the manufacture method according to the present disclosure has strong physical properties of being readily applicable to the mask pack production process using water. The method has an effect of high economic efficiency, since a mask pack having excellent heavy metal adsorption performance can be manufactured by surface modification of the mask pack, in spite of not separately adding an expensive material capable of adsorbing heavy metals.

BRIEF DESCRIPTION OF DRAWINGS

FIG. 1 is an exemplary schematic diagram illustrating an overall process of a method for manufacturing a mask pack for heavy metal adsorption according to the present disclosure;

FIG. 2 is a graph showing a moisture evaporation rate over time of the mask pack manufactured by the method according to the present disclosure;

FIG. 3 shows scanning electron microscope (SEM) images of Examples 1 and 2 and Comparative Examples 1 and 2; and FIG. 4 shows a wet mask pack for heavy metal adsorption manufactured in Example 2.

DETAILED DESCRIPTION OF THE INVENTION

Hereinafter, the present disclosure will be described in more detail.

When a component is referred to as "comprising" an element in the specification, it is understood that the component may comprise another element and does not preclude the presence or addition thereof, unless specifically stated otherwise.

The present disclosure relates to a method for manufacturing a mask pack for heavy metal adsorption comprising immersing a cellulose nonwoven fabric in an alkali solution by a cold pad batch method and then aging the cellulose nonwoven fabric at room temperature for 10 minutes to 50 minutes, and immersing the cellulose nonwoven fabric in a carboxymethylation solution by the cold pad batch method, and then aging the cellulose nonwoven fabric at room temperature to 60° C. or less for 10 minutes to 3 hours.

In the method for manufacturing a mask pack for heavy metal adsorption according to the present disclosure, carboxymethylation reactivity of the cellulose can be improved by primarily immersing the nonwoven fabric in an alkali solution and then aging, followed by secondarily immersing the nonwoven fabric in a carboxymethylation solution and then aging.

The conventional method of manufacturing mask packs by adding a substance capable of adsorbing heavy metals to a nonwoven fabric has a limitation in increasing heavy metal adsorption performance, and when a large amount of the above substance is added, the original characteristics of the mask pack may be deteriorated. In addition, there are problems in that a substance capable of adsorbing heavy metals is expensive and use of an excessive amount of such a substance is thus not economical.

In the case of manufacturing the mask pack by the method according to one embodiment of the present disclosure, although a substance capable of adsorbing heavy metals is not separately added to the nonwoven fabric, the surface of the cellulose fiber is modified through a carboxymethylation reaction to improve heavy metal adsorption performance, and mass production is possible to increase production process efficiency and to manufacture a mask pack capable of adsorbing heavy metals by an economical method.

In the present disclosure, the cold pad batch method refers to a method comprising continuous processing of squeezing at an appropriate pressure immediately after immersing a fiber material in a solution, and then reacting at a low temperature while aging for a certain period of time. The present disclosure can increase production process efficiency by manufacturing the mask pack using the cold pad batch method.

In one embodiment of the present disclosure, the alkali solution may further contain sodium hydroxide in addition to a solvent consisting of water and alcohol in a weight ratio of 10:5 to 10:8.

In one embodiment of the present disclosure, the concentration of the alkali solution is preferably 5 to 15%, more preferably 8 to 12%. When the concentration is less than 5%, the desired substitution degree cannot be obtained through carboxymethylation and when the concentration exceeds 15%, the substitution degree through carboxymethylation may be excessively high and side reaction between an acid and an alkali may occur.

In this disclosure, "%" means "wt %".

In one embodiment of the present disclosure, the carboxymethylation solution may further contain monochloroacetic acid in addition to a solvent consisting of water and alcohol in a weight ratio of 1:10 to 4:10.

The carboxymethylation solution may be a 10% monochloroacetic acid solution in which monochloroacetic acid is dissolved in a solvent containing 20% of water and 80% of alcohol.

The alcohol may be alone or in a mixture form selected from the group consisting of alcohols having 1 to 4 carbon atoms. The alcohol may be ethanol, methanol or isopropanol, and preferably is isopropanol, but the present disclosure is not limited thereto.

In one embodiment of the present disclosure, the alcohol is selected from the group consisting of ethanol, methanol and isopropanol.

In one embodiment of the present disclosure, the alcohol may be alone or in a mixture form selected from the group consisting of ethanol, methanol, and isopropanol.

As herein used, the term "carboxymethylation" refers to substitution of a hydroxyl group (celluose-OH) substituted in the C6 of the glucose moiety constituting cellulose (celluose-O—$CH_2COOH$), by a carboxymethyl group (—$CH_2COOH$).

In one embodiment of the present disclosure, when the cold pad batch method is conducted using an alkali solution, the aging temperature may be room temperature. In general, when the aging temperature is lower than room temperature, the reaction cannot be sufficiently performed, and when the aging temperature is higher than room temperature, the reaction rate is fast and thus uniform substitution degree cannot be obtained over the entire area of the nonwoven fabric through carboxymethylation. The present disclosure comprises squeezing before aging, thereby providing a uniform reaction at a temperature higher than room temperature.

In the present disclosure, "room temperature" means "20±5° C.".

In one embodiment of the present disclosure, when the cold pad batch method is conducted using an alkali solution, the aging time may be 10 to 50 minutes, preferably 25 to 35 minutes. When the aging time is less than 10 minutes, sufficient aging by the alkali solution cannot be performed, and when the aging time exceeds 50 minutes, the physical properties of the mask pack manufactured by excessive aging may be weakened.

In one embodiment of the present disclosure, when the cold pad batch method is conducted using a carboxymethylation solution, the aging temperature may be room temperature to 60° C., preferably, room temperature to 55° C. When the aging temperature is lower than room temperature, the carboxymethylation reaction cannot be sufficiently performed, and when the aging temperature is higher than 60° C., the mask pack is excessively aged due to high temperature, has weakened physical properties and thus may be readily broken.

In one embodiment of the present disclosure, when the cold pad batch method is conducted using a carboxymethylation solution, the aging time may be 10 minutes to 3 hours, preferably 1 hour to 2 hours. When the aging time is less than 10 minutes, the carboxymethylation reaction by the carboxymethylation solution cannot be sufficiently performed, and the content of the carboxymethyl group in the cellulose may be excessively low. When the aging time exceeds 3 hours, the mask pack is excessively aged, has weakened physical properties and thus may be readily torn or damaged.

In one embodiment of the present disclosure, the manufacturing method of the mask pack for heavy metal adsorption may further comprise washing with water and filtering. By washing with water and filtering, the physical properties of the manufactured mask pack can be further reinforced.

The method for manufacturing a mask pack according to the present disclosure may further comprise drying the mask pack that has undergone the washing and filtering processes. The drying temperature may be 30 to 50° C., preferably 35 to 55° C. When the drying temperature is lower than 30° C., drying of the mask pack cannot be sufficiently performed, and when the drying temperature exceeds 50° C., the mask pack may be shrunken and have deteriorated elasticity due to high temperature.

In one embodiment of the present disclosure, the method for manufacturing a mask pack for heavy metal adsorption may further comprise squeezing using a rubber roller after immersing in the alkaline solution or the carboxymethylation solution and before aging. The rubber roller enables the alkali solution or the carboxymethylation solution to uniformly permeate into the cellulose nonwoven fabric and the carboxymethylation reaction to be effectively conducted.

In the present disclosure, the mask pack for heavy metal adsorption may comprise carboxymethylcellulose fibers having a carboxylate content of 0.10 mmol/g to 0.58 mmol/g. The mask pack satisfying the range defined above has excellent heavy metal adsorption capability, and is easy to handle and store. When the carboxylate content is less than 0.10 mmol/g, the heavy metal adsorption capability of the mask pack is lowered. When the carboxylate content is higher than 0.58 mmol/g, the carboxymethylated cellulose is melted in a wet state, so that the mask pack may not be usable. The carboxylate content can be controlled by optimizing the aging temperature and the aging time in accordance with the cold pad batch method of the present disclosure. Although carboxylate is introduced into cellulose, morphological change of cellulose fibers does not occur before/after the introduction of the carboxylate as shown in FIG. 3.

In the present disclosure, the carboxylate content can be measured by the method described later. A 250 mL beaker containing 0.6 g of a ground sample, 2 mL of 0.1 M NaCl and the balance of deionized water to a total of 200 g is prepared. The pH of the CNF is adjusted to 3 by adding 0.1M HCl while stirring the suspension. 0.5 mL of 0.05 M NaOH is added to the CNF (pH=3) suspension and stirred, and the conductivity is recorded. The point (V1) at which conductivity broadens after it decreases and then the point (V2) at which conductivity rapidly increases are determined. The content of the acidic group is calculated by the following Equation 1:

$$[\text{Acidic group}] = \frac{[(V2-V1) \times C_{NaOH}]}{m_{sample}} \text{ (mmol/kg)}$$

wherein V1, V2=volume of NaOH (ml),
$C_{NaOH}$=NaOH concentration (mol L$^{-1}$)
$m_{sample}$=Dry weight of the sample (kg)

In one embodiment of the present disclosure, the nonwoven fabric may be a nonwoven fabric made of cellulose. The nonwoven fabric may be a high-density cellulose nonwoven fabric such as Tencel or Bemliese, but the present disclosure is not limited thereto.

The present disclosure provides a mask pack for heavy metal adsorption manufactured by the above-described manufacturing method.

An embodiment of the present disclosure provides a mask pack for heavy metal adsorption having a heavy metal adsorption amount of 4 to 11 mg/g.

The mask pack for heavy metal adsorption may have a heavy metal adsorption amount (mg) of 4 to 11 mg/g per dry weight (g) of the cellulose nonwoven fabric material. Specifically, the heavy metal adsorption amount may be 4.3 to 10.15 mg/g.

In this disclosure, the heavy metal may be copper (Cu) or lead (Pb). The copper (Cu) may be adsorbed as copper sulfate (CuSO$_4$), and the lead (Pb) may be adsorbed as lead chloride (PbCl$_2$). Specifically, among the heavy metals, the amount of copper (Cu) adsorbed is 4 to 11 mg/g, and the amount of lead (Pd) absorbed is 7 to 9 mg/g. More specifically, among the heavy metals, the amount of copper (Cu) adsorbed may be 4.3 to 10.15 mg/g and the amount of lead (Pd) adsorbed may be 7.8 to 8 mg/g.

Taking into consideration the fact that the maximum amount of heavy metals adsorbed on an adult face is about 1 mg per day, when the mask pack for heavy metal adsorption according to the present disclosure is used, the heavy metal adsorbed on the face can be sufficiently adsorbed.

The heavy metal adsorption amount can be measured using an ICP device. The ICP device is an apparatus that is capable of using inductively coupled plasma mass spectroscopy (ICP MS). In one embodiment of the present disclosure, ICP-OES (Optima 7300DV) may be used for measurement of the heavy metal adsorption amount.

In the present disclosure, the mask pack is used to supply nutrition, moisture and the like to the face. In general, the mask pack, which comprises a cosmetic ingredient such as skin toner impregnated in a substrate such as a nonwoven fabric, is attached to the skin for a certain period of time so that the cosmetic ingredient may be delivered to the skin, and then removed therefrom after the certain period of time. The mask pack can be used not only a part of for the face or the body such as the neck, shoulder, arm or leg as well as the whole body. The cosmetic ingredient such as skin toner may contain water as well as a moisturizer, a surfactant, a thickener, a preservative, a perfume, an oil or the like. In addition, any cosmetic ingredient may be used without particular limitation as long as it can improve skin care functions in the related art such as moisturizing, whitening, anti-aging, lifting and soothing.

In the present disclosure, the shape of the mask pack may be variously determined depending on the area of the skin to which the mask pack is attached. Generally, the shape of the mask pack has a configuration in which regions corresponding to the eye and the mouth are opened and the mask pack is manufactured such that the shape thereof corresponds to the shape of the face, as shown in FIG. 4. In addition, mask packs used exclusively for eyes, nose or lips may be present and the shapes thereof are not particularly limited. The mask pack may have a planar or three-dimensional structure.

FIG. 1 is a schematic diagram illustrating an overall process of a method for manufacturing a mask pack for heavy metal adsorption according to the present disclosure. Specifically, a nonwoven fabric is immersed in an alkali solution using a guide roller (step 1), and then the alkali solution sucked in the nonwoven fabric is squeezed using a rubber roller (step 2) to efficiently permeate the alkali solution into the nonwoven fabric. Then, the nonwoven fabric treated with the alkali solution is aged at room temperature for 10 to 50 minutes (step 3).

Then, the nonwoven fabric is immersed in a carboxymethylation solution using a guide roller (step 4), and then the carboxymethylation solution sucked into the nonwoven fabric is squeezed using a rubber roller (step 5) to efficiently permeate the carboxymethylation solution into the nonwoven fabric. Then, the nonwoven fabric treated with the carboxymethylation solution is aged at a temperature of room temperature to 60° C. or less for 10 minutes to 3 hours (step 6). Thereafter, the nonwoven fabric is washed with water by immersion (step 7), and then is squeezed using a rubber roller (step 8). Subsequently, the nonwoven fabric is filtered with water (step 9) and dried at 40° C. (step 10) to manufacture a mask pack for heavy metal adsorption.

The tensile strength in the wet state of the heavy metal adsorption mask pack manufactured by the manufacturing method according to the present disclosure may be 3 to 7 MPa. Specifically, the tensile strength may be 3.42 to 6 MPa. More specifically, the tensile strength may be 4.34 to 6 MPa. When the tensile strength satisfies the range defined above, physical properties of the mask pack are strong even in the dry state as well as in the wet state, and the shape of the mask pack can be maintained well and thus the mask pack may not be readily damaged. The tensile strength can be controlled by optimizing the aging temperature and the aging time according to the cold pad batch method of the present disclosure.

The tensile strength in a wet state of the mask pack for heavy metal adsorption can be measured on a sample of the mask pack according to the present disclosure using a universal testing machine (UTM). When using the universal testing machine (UTM), the tensile strength can be measured under conditions of a length of 3 cm and a speed of 10 mm/min. Also, the sample can be prepared with the width× length of 2 cm×5 cm by immersing the mask pack according to the present disclosure in tap water and storing the same at 30° C. for 3 days.

The moisture evaporation rate of the heavy metal adsorption mask pack manufactured by the manufacturing method of the present disclosure is 60% or less at 15 minutes. Preferably, the moisture evaporation rate may be 20% or less at 15 minutes. As another example, the moisture evaporation rate may be more than 0% and not more than 20% at 15 minutes. As another example, the moisture evaporation rate may be 1% or more and 20% or less at 15 minutes. In another embodiment of the present disclosure, the moisture evaporation rate is 20% or less at 15 minutes, 35% or less at 30 minutes, 52% or less at 45 minutes and 65% or less at 60 minutes. Preferably, the moisture evaporation rate is more than 0% and not more than 20% at 15 minutes, is more than 0% and not more than 35% at 30 minutes, is more than 0% and not more than 52% at 45 minutes, and is more than 0% and not more than 65% at 60 minutes. More preferably, the moisture evaporation rate is 1% or more and 20% or less at 15 minutes, 21% or more and 35% or less at 30 minutes, 36% or more and 52% or less at 45 minutes, and 53% or more and 65% or less at 60 minutes. In another embodiment, the moisture evaporation rate is 1% or more and 19% or less at 15 minutes, 20% or more and 30% or less 30 minutes, 31% or more and 45% or less at 45 minutes, and 46% or more and 56% or less at 60 minutes. The mask pack that contains cellulose having an increased carboxylate content due to the carboxymethylation reaction becomes highly hydrophilic and has a low moisture evaporation rate over time because it retains water well. Thus, the mask pack according to one embodiment of the present disclosure has high capability to adsorb heavy metals and excellent moisturizing effect. The moisture evaporation rate is measured by impregnating the mask pack in water for 1 hour or more and then measuring the rate of change in weight with respect to the initial weight on an hourly basis in an incubator at a humidity of 60% at 30° C. Specifically, the moisture evaporation rate can be calculated using the following equation.

$$\text{Moisture evaporation rate (\%)} = \frac{(\text{Initial wet weight} - \text{Late wet weight})}{\text{Initial wet weight}} * 100$$

The feature that the moisture evaporation rate is 60% or less at 15 minutes means that the moisture evaporation rate of the mask pack measured after allowing the mask pack for heavy metal adsorption manufactured by the manufacturing method of the present disclosure to stand for 15 minutes is 60% or less. This description applies to the moisture evaporation rate.

Hereinafter, the present disclosure will be described in detail with reference to examples. However, the following examples of the present disclosure may be embodied in different forms and should not be construed as limiting the scope of the present disclosure. The examples are provided only to offer more thorough and complete understanding of the disclosure to those having ordinary knowledge in the art.

EXAMPLE 1

1. Performing Cold Pad Batch Method Using Alkali Solution

Sodium hydroxide (NaOH) was added to a solvent obtained by mixing water and isopropanol in a weight ratio of 6:4 to prepare a 10% alkali solution. A cellulose nonwoven fabric was immersed in the alkali solution for 1 minute and then the nonwoven fabric was squeezed using a rubber roller. Then, the nonwoven fabric was aged at room temperature for 30 minutes.

2. Performing Cold Pad Batch Method Using Carboxymethylation Solution

Monochloroacetic acid was added to a solvent obtained by mixing water and isopropanol in a ratio of 2:8 to prepare a 10% carboxymethylated solution (monochloroacetic acid solution). The nonwoven fabric that had been immersed in the alkali solution and aged was immersed in the carboxymethylation solution for 5 minutes and then was squeezed using a rubber roller. Then, the nonwoven fabric was aged at room temperature for 3 hours.

3. Washing With Water, Filtering and Drying

The nonwoven fabric that had been immersed in the carboxymethylation solution and aged was washed with water and filtered. Then, the nonwoven fabric was dried in an oven at 40° C. to manufacture a mask pack for heavy metal adsorption.

EXAMPLE 2

A mask pack was manufactured in the same manner as in Example 1, except that the aging temperature of the nonwoven fabric was 50° C. and the aging time thereof was 30 minutes in the step of 2. performing cold pad batch method using carboxymethylation solution of Example 1. FIG. 4 shows the state of the manufactured mask pack.

EXAMPLE 3

A mask pack was manufactured in the same manner as in Example 2, except that filtering was not performed in the step of 3. Washing, filtering and drying of Example 2.

COMPARATIVE EXAMPLE 1

A mask pack was manufactured in the same manner as in Example 1, except that the aging temperature was 80° C. and the aging time was 30 minutes in the step of 2. Performing cold pad batch method using carboxymethylation solution of Example 1.

COMPARATIVE EXAMPLE 2

The cellulose nonwoven fabric was immersed in water at room temperature for 30 minutes and aged for 1 hour. Then, the cellulose nonwoven fabric was dried in an oven at 40° C.

COMPARATIVE EXAMPLE 3

A mask pack was manufactured in the same manner as in Example 1, except that the aging temperature of the nonwoven fabric was 50° C. and the aging time thereof was 3 hours and 30 minutes in the step of 2. performing cold pad batch using carboxymethylation solution of Example 1, and filtering was not performed in the step of 3. Washing with water, filtering and drying.

The conditions applied to the aforementioned Examples and Comparative Examples are shown in Table 1 below. Scanning electron microscope (SEM) images of the surfaces of the mask packs manufactured in Examples 1 and 2 and Comparative Examples 1 and 2 are shown in FIG. 3.

TABLE 1

|  | Aging temperature for cold pad batch method using carboxymethylation solution | Aging time for cold pad batch method using carboxymethylation solution | Presence or absence of filtering |
|---|---|---|---|
| Example 1 | Room temperature | 1 hour | ○ |
| Example 2 | 50° C. | 30 minutes | ○ |
| Example 3 | 50° C. | 30 minutes | X |

TABLE 1-continued

|  | Aging temperature for cold pad batch method using carboxymethylation solution | Aging time for cold pad batch method using carboxymethylation solution | Presence or absence of filtering |
|---|---|---|---|
| Comparative Example 1 | 80° C. | 30 minutes | ○ |
| Comparative Example 2 | — | — | — |
| Comparative Example 3 | 50° C. | 3 hours 30 minutes | X |

Test example.

The tensile strengths and heavy metal adsorption amounts of the mask packs manufactured according to Examples and Comparative Examples above were measured. The nonwoven fabrics modified under respective conditions of Examples and Comparative Examples were immersed in tap water for 3 days at 30° C., and then cut to a width of 2 cm and a length of 5 cm to prepare samples. At this time, the nonwoven fabrics were cut so as to measure the physical properties in the longitudinal (MD) direction.

1. Measurement of Physical Properties (Tensile Strength in Wet State) of Mask Packs for Heavy Metal Adsorption The prepared samples were measured for wet-tensile strength using a universal testing machine (UTM). The measurement length was 3 cm and the rate was 10 mm/min. The wet tensile strengths of the samples manufactured respectively according to Examples and Comparative Examples are shown in Table 2 below.

2. Measurement of Heavy Metal Adsorption Amount of Mask Packs for Heavy Metal Adsorption (1) Method for Heavy Metal (Lead) Adsorption 1.34 g of lead chloride ($PbCl_2$) was dissolved in 1 L of water to prepare a lead chloride stock solution (1,000 mg/l ($Pb^{2+}$)). A lead chloride stock solution (pH 4.1) was diluted to prepare an aqueous lead chloride solution (50 mg/l). The mask packs manufactured in Examples and Comparative Examples were immersed in 40 g of the prepared aqueous lead chloride solution (50 mg/l) for 24 hours.

(2) Method for Heavy Metal (Copper) Adsorption 2.512 g of copper sulfate ($CuSO_4$) was dissolved in 1 L of water to prepare a copper sulfate stock solution (1,000 mg/l ($Cu^{2+}$)). The copper sulfate stock solution (pH 4.3) was diluted to prepare an aqueous copper sulfate solution (100 mg/l). The mask packs manufactured according to Examples and Comparative Examples were immersed in 40 mg of the prepared 50 mg/l aqueous copper sulfate solution for 24 hours.

(3) Method for Measuring Heavy Metal Adsorption Amount

The adsorbed aqueous solution was filtered using a polytetrafluoroethylene (PTFE) filter. 1 g of the filtered sample (aqueous solution) was charged in a 15 ml coning tube. 100 μL of scandium (Sc) as an internal standard material was added to the coning tube, and the solution was diluted with ultrapure water to adjust the total solution volume to 10 mL. After dilution, the resulting solution was filtered again using a polytetrafluoroethylene (PTFE) filter. After preparing standard solutions at 1 μg/mL, 5 μg/mL and 10 μg/mL, the amount of heavy metal adsorption was analyzed by ICP-OES (Optima 7300DV).

(4) Method of Calculating Heavy Metal Adsorption Amount

The heavy metal adsorption amount of the manufactured mask pack was calculated in accordance with the following equation and the results are shown in Table 2 below:

$$\text{Adsorption capacity (mg/g)} = \frac{(C_i - C_f)V}{M} \text{(mg/g)} \quad \text{[Equation]}$$

wherein adsorption capacity (mg/g) represents an amount (mg) of heavy metal ion adsorbed per 1 g of an adsorbent, Ci represents an initial concentration (mg/L) of aqueous lead chloride or copper sulfate solution before heavy metal adsorption;

Cf represents a final concentration (mg/L) of aqueous solution after filtration of aqueous solution upon completion of heavy metal adsorption;

V represents an initial solution volume used for the test;

M represents a weight of a non-woven fabric (adsorbent dose, g).

TABLE 2

|  | Tensile strength of wet mask pack | Heavy metal adsorption amount (mg/g) | |
|---|---|---|---|
|  | (MPa) | $CuSO_4$ | $PdCl_2$ |
| Example 1 | 6.00 | 4.3 | 7.8 |
| Example 2 | 4.34 | 10.15 | 8.0 |
| Example 3 | 3.42 | 9.08 | 8.0 |
| Comparative Example 1 | 0.91 | 12.77 | 8.0 |
| Comparative Example 2 | 7.53 | 1.1 | 3.2 |
| Comparative Example 3 | — | — | — |

As can be seen from Table 2 above, Examples 1 to 3 had higher wet-tensile strength of the mask packs and thus had better mechanical properties, as compared to Comparative Example 1. Further, it can be seen that the mask packs manufactured by Examples 1 to 3 had higher heavy metal adsorption amounts than those of Comparative Example 2, which means that the mask packs manufactured by the present disclosure had excellent mechanical properties and higher heavy metal adsorption amounts. In Comparative Example 3, the wet-tensile strength and the heavy metal adsorption amount of the mask pack could not be measured because the physical properties were so weak that the structure of the mask pack collapsed in a wet state, which is indicated by "-" in Table 2 above.

1. Measurement of Moisture Evaporation Rate of Mask Pack for Heavy Metal Adsorption The mask packs manufactured according to Examples and Comparative Examples were each immersed in water for 1 hour or more. Then, the rate of change in weight with respect to the initial weight was measured on an hourly basis in an incubator at 30° C. and a humidity of 60%. Specifically, the moisture evaporation rate was calculated in accordance with the following equation and the results are shown in Table 3 below.

$$\text{Moisture evaporation rate (\%)} = \frac{\text{(Initial wet weight} - \text{Late wet weight)}}{\text{Initial wet weight}} * 100 \quad \text{[Equation]}$$

TABLE 3

| | Moisture evaporation rate (%) | | | |
| --- | --- | --- | --- | --- |
| | 15 minutes | 30 minutes | 45 minutes | 60 minutes |
| Example 1 | 18.9 | 29.7 | 45.0 | 56.0 |
| Example 2 | 16.6 | 27.9 | 41.9 | 51.3 |
| Example 3 | 19.9 | 35.0 | 51.2 | 64.7 |
| Comparative Example 1 | 11.4 | 21.2 | 30.0 | 38.5 |
| Comparative Example 2 | 24.4 | 43.6 | 62.5 | 76.9 |
| Comparative Example 3 | — | — | — | — |

The moisture evaporation rates over time of the mask packs for heavy metal adsorption manufactured by the manufacturing method according to the present disclosure are shown as a graph of FIG. 2, based on the results shown in Table 3 above. As can be seen from Table 3 and FIG. 2, Examples 1 to 3 had lower moisture evaporation rates over time and thus better moisturizing effect, as compared to Comparative Example 2.

Meanwhile, Comparative Example 1 had lower moisture evaporation rate as compared to Examples 1 to 3, but Comparative Example 1 had much lower tensile strength of the mask pack and thus lower mechanical strength than those of Examples 1 to 3, as can be seen from Table 2.

Also, the weight of the mask pack for measuring the moisture evaporation rate could not be measured, since the mask pack of Comparative Example 3 was partially dissolved in water in the water absorption process.

Accordingly, it can be seen that the mask pack according to the manufacturing method of the present disclosure has excellent mechanical strength, and sufficient heavy metal adsorption capability and moisturizing effect, and mask packs capable of adsorbing heavy metals can be mass-produced by an economic method.

Although preferred embodiments of the present disclosure have been described in detail, it will be appreciated by those skilled in the art that modifications and alterations are possible in these embodiments without departing from the spirit of the disclosure, the scope of which is defined in the appended claims and their equivalents.

DESCRIPTION OF REFERENCE NUMERALS

1: Immersing in alkali solution
2: Squeezing alkali solution sucked in nonwoven fabric using rubber roller
3: Aging nonwoven fabric treated with alkali solution
4: Immersing in carboxymethylation solution
5: Squeezing carboxymethylation solution sucked in nonwoven fabric using rubber roller
6: Aging nonwoven fabric treated with carboxymethylation solution
7: Washing with water by immersion
8: Squeezing using rubber roller
9: Filtering with water
10: Drying

The invention claimed is:

1. A method for manufacturing a mask pack for heavy metal adsorption comprising:
    immersing a cellulose nonwoven fabric in an alkali solution according to a cold pad batch method and then aging the cellulose nonwoven fabric at room temperature for 10 minutes to 50 minutes; and
    immersing the cellulose nonwoven fabric in a carboxymethylation solution according to the cold pad batch method and then aging the cellulose nonwoven fabric at room temperature to 60° C. for 10 minutes to 3 hours.

2. The method of claim 1, further comprising washing the cellulose nonwoven fabric with water and filtering the cellulose nonwoven fabric.

3. The method of claim 1, wherein the alkali solution further comprises sodium hydroxide in addition to a solvent consisting of water and alcohol in a weight ratio of 10:5 to 10:8 of water to alcohol.

4. The method of claim 1, wherein the carboxymethylation solution comprises monochloroacetic acid in addition to a solvent consisting of water and alcohol in a weight ratio of 1:10 to 4:10 of water to alcohol.

5. The method of claim 1, further comprising squeezing the cellulose nonwoven fabric using a rubber roller after immersing in the alkaline solution or the carboxymethylation solution and before aging.

6. The method of claim 3, wherein the alcohol is at least one alcohol selected from ethanol, methanol and isopropanol.

7. The method of claim 1, wherein the mask pack comprises carboxymethylcellulose fibers having a carboxylate content of 0.10 mmol/g to 0.58 mmol/g.

8. A mask pack for heavy metal adsorption manufactured by the method of claim 1.

9. The mask pack of claim 8, wherein the mask pack has a heavy metal adsorption amount of 4 to 11 mg/g.

10. The mask pack of claim 8, wherein the mask pack has a wet-tensile strength of 3 to 7 MPa.

11. The mask pack of claim 8, wherein the mask pack has a moisture evaporation rate of 60% or less at 15 minutes.

12. The method of claim 1, wherein the alkali solution has a concentration of 5 to 15%.

13. The method of claim 4, wherein the carboxymethylation solution is a 10% monochloroacetic acid solution comprising monochloroacetic acid in a solvent containing 20% of water and 80% of alcohol.

14. The method of claim 4, wherein the alcohol is at least one alcohol selected from ethanol, methanol and isopropanol.

* * * * *